United States Patent [19]

Grollier et al.

[11] Patent Number: 4,735,797

[45] Date of Patent: Apr. 5, 1988

[54] COSMETIC COMPOSITION FOR DELAYING THE APPEARANCE OF AN OILY ASPECT OF HAIR

[75] Inventors: Jean-François Grollier; Chantal Fourcadier, both of Paris, France

[73] Assignee: L'Oreal, Paris, France

[21] Appl. No.: 747,443

[22] Filed: Jun. 21, 1985

[30] Foreign Application Priority Data

Jun. 22, 1984 [LU] Luxembourg ............................ 85427

[51] Int. Cl.⁴ .......................... A61K 7/06; A61K 7/42; A61K 7/44; A61K 9/12
[52] U.S. Cl. ............................. 424/47; 424/DIG. 4; 424/59; 424/60; 424/70; 424/78; 528/328
[58] Field of Search .................... 528/328; 424/78, 70, 424/47, DIG. 4

[56] References Cited

U.S. PATENT DOCUMENTS

| | | | |
|---|---|---|---|
| 3,387,070 | 6/1968 | Wakapa et al. | 528/328 X |
| 3,499,874 | 3/1970 | Takahashi et al. | 528/328 X |
| 3,927,204 | 12/1975 | Neri et al. | 528/328 X |

FOREIGN PATENT DOCUMENTS

| | | | |
|---|---|---|---|
| 2132241 | 11/1972 | France | 424/70 |
| 2403076 | 4/1979 | France | 424/70 |
| 2424292 | 11/1979 | France | 424/70 |
| 2508795 | 11/1983 | France | 424/47 |

*Primary Examiner*—Dale R. Ore
*Attorney, Agent, or Firm*—Cushman, Darby & Cushman

[57] ABSTRACT

A cosmetic composition for application to the hair to delay the appearance of an oily aspect of the hair contains a water-soluble polymer of the poly-$\beta$-alanine type.

7 Claims, No Drawings

COSMETIC COMPOSITION FOR DELAYING THE APPEARANCE OF AN OILY ASPECT OF HAIR

The present invention relates to a new cosmetic composition for delyaing the appearance of an oily aspect of the hair. These compositions contain at least one particular water-soluble polyamide.

The invention also relates to the use of this particular polyamide in the treatment of hair in order to delay the appearance of an oily aspect.

Belgian Pat. No. 893,738 describes the use of water-soluble polyamides of the poly-$\beta$-alanine type in cosmetic compositions for hair. These compositions impart volume to the hair as well as good holding properties so as to facilitate obtaining bouffant hair styles.

In subsequent research involving these water-soluble polyamides, it has now been discovered that certain ones of these polyamides are capable of delaying the appearance of an oily aspect of hair. This appearance of an oily aspect, which is observed in a significant number of individuals, is due to the well known phenomenon of "re-oiling", that is to say, to the secretion of sebum by the sebaceous glands. In short these individuals are characterized as having "oily" hair.

The present invention thus relates to a new cosmetic composition for the hair to delay the appearance of an oily aspect of the hair, said composition comprising, as the active component, at least one water-soluble polyamide of the poly-$\beta$-alanine type.

It is appropriate to note that the compositions of the present invention do not appear to act on the production of sebum but act only on the appearance of the hair, which takes on less rapidly an "oily" aspect notwithstanding the re-oiling phenomenon.

The present invention relates principally to cosmetic compositions such as defined above, characterized by the fact that they contain, as the active component, at least one water-soluble polyamide containing from 50 to 100% of units of formula I:

$$-[CH_2-CH_2-CO-NH]-\quad (I)$$

and from 0 to 50% of units of formula II:

$$-[CH_2-CH]-\quad (II)$$
$$\quad |$$
$$\quad CONH_2$$

The water-soluble polyamides of the poly-$\beta$-alanine type (called hereinafter "poly-$\beta$-alanines") are described in U.S. Pat. No. 4,082,730 and in Belgian Pat. No. 893,738 or they can be obtained in accordance with methods analogous to those described in these patents.

The water-soluble poly-$\beta$-alanines used in the compositions of the present invention generally have a molecular weight ranging from 500 to 200,000, preferably from 2,000 to 100,000 and more particularly from 50,000 to 100,000, the molecular weight being determined according to a light diffusion method.

It has been noted that when the re-oiling phenomenon is significant, it is necessary to use relatively large amounts of the composition containing a high concentration of the poly-$\beta$-alanines.

But this increase in applied dosage, which is necessary to obtain the desired effect, involves a reduction of other cosmetic properties of the product, in particular during repeated applications.

In effect it has been noted that repeated application of these compositions, containing high concentrations of polymer based on poly-$\beta$-alanine, has a tendency to leave on the hair a deposit which is preceptible to the touch. From this it results that the application of high concentrations of poly-$\beta$-alanine certainly permits a delay in the appearance of an oily aspect of hair but, at length, it also imparts to the hair style a less esthetic appearance.

It has now been disclovered that it is possible to obtain compositions which are capable of delaying the appearance of an oily aspect of hair, without experiencing the above noted disadvantages if the poly-$\beta$-alanine is employed in combination with certain other hair treating agents, and in particular with at least one polyaspartic acid derivative such as those described in French Pat. No. 77.27769 (Publication No. 2.403.076).

These polyaspartic acid derivatives have previously been proposed as adjuvants in capillary compositions because they improve the hold of the hair.

These polysparatic acid derivative have the following formula III:

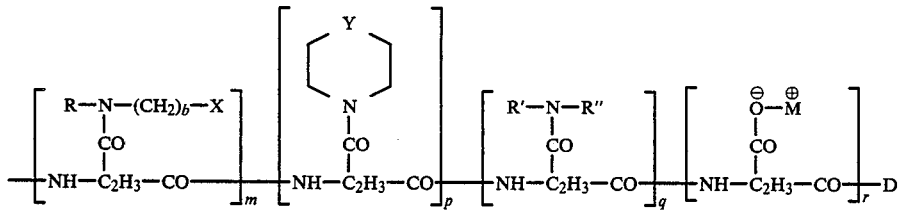

wherein
R represents hydrogen or lower alkyl,
b is a whole number ranging from 2 to 6,
X represents $-NR_I(R_{II})$ or $-\oplus N-R_I(R_{II})(R_{III})Z^\ominus$, wherein $R_I$, $R_{II}$ and $R_{III}$ each independently represent hydrogen, alkyl having 1-18 carbon atoms or alkenyl having at most 18 carbon atoms, or indeed $R_I$ and $R_{II}$ together, with the nitrogen atom to which they are attached, represent a ring with 6 chains and capable of containing another heteroatom, and $Z^\ominus$ represents an anion derived from an organic or mineral acid;
Y represents oxygen, methylene, $-N(R''')$ or $\oplus -N(R''')(R'''')Z_1^\ominus$, wherein $R'''$ and $R''''$ each independently represent hydrogen, alkyl having 1-18 carbon atoms or alkenyl having at most 18 carbon atoms and $Z_1^\ominus$ represents an anion derived from an organic or mineral acid;
R' represents hydrogen, lower hydroxyalkyl, lower hydroxyalkyloxyalkyl, alkyl having 1-18 carbon atoms or alkenyl having at most 18 carbon atoms;
R'' represents hydrogen, lower hydroxyalkyl or lower alkyl;

M represents hydrogen, alkali metal or ½ alkaline earth metal atom, or indeed M⊕ represents an ammonium ion derived from an amine of the formula

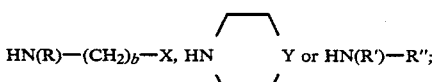

D represents

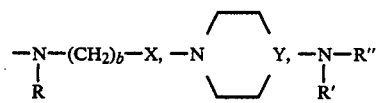

or —O⊖M⊕;

m, p, q and r represent whole numbers, including zero, such that the sum, (m+p+q+r), ranges from 15 to 500, m and p being equal to zero simultaneously only in the following cases:

(a) when q is other than zero and R' represents hydroxyalkyl; and
(b) when q is equal to zero.

Representative polyaspartic acid derivatives of Formula III include those for which:

(a) m=p=O, R'=H, R"=—CH₂—CH₂—OH, and D=—O⊖M⊕ wherein M⊕ is a cation derived from monoethanolamine;
(b) m=p=q=O, D=—O⊖M⊕ wherein M⊕ represents H⊕, an alkali metal cation or a cation derived from monoethanolamine or 2-amino-2-methyl-1-proponol; and
(c) m=q=r=O,

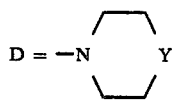

wherein Y=—O—, —CH₂ or —N(CH₃)—.

These polymers can be prepared principally according to procedures analogous to those described in French Pat. Nos. 2.403.076 and 2.424.292.

In the compositons of the present invention the amount of the polymer of the poly-β-alanine type can vary generally from 0.1 to 5%, and in particular from 0.5 to 2%, by weight, based on the total weight of the composition.

The amount of the polyaspartic acid derivative can vary from 0 to 5% by weight; generally when it is present, its concentration varies from 0.1 to 5%, and in particular, from 0.2 to 2% by weight, based on the total weight of the composition.

The carrier present in the composition of the invention is a conventional liquid carrier capable of dissolving the active components employed. Perferably there is employed an aqueous carrier comprising water or a hydroalcoholic mixture, the alcohol being, preferably, an alkanol having 1–4 carbon atoms, and in particular ethanol or isopropyl alcohol.

When the carrier is a hydroalcoholic mixture, the alcohol is present generally in an amount lower than 55% by weight, relative to the total weight of the composition.

The compositions of the present inventions can also contain at least one conventional adjuvant such as perfumes, coloring agents, preservatives, pH modifiers, softening agents, sequesterants, foam stabilizers, U.V. absorbers, peptizing agents, surfactants, and the like, so as to provide the desired form thereof for a given use. These compositons are employed as rinse or non rinse products.

The present invention particularly relates to new industrially packaged cosmetic compositions comprising a composition such as defined above, in combination with an appropriate package and with a use label containing written instructions for using the composition so as to delay the appearance of an oily aspect of the hair.

These compositions are provided principally in the form of non-rinse products such as lotions, styling foams, forming lotions, setting lotions or brushing lotions, which are prepared according to conventional procedures.

The compositions of the present invention can also be provided in the form of shampoos, rinsing lotions, treating products that can be applied before or after coloring or bleaching the hair, before or after shampooing the hair, or before or after permanently waving the hair.

The pH of the composition of the present invention can range from 3 to 10.

These compositions can also be provided in the form of pressurized compositions for aerosols, sprays or foams, in combination with a propellant. There can be employed, as a propellant, CO₂, nitrogen, nitrous oxide, volatile hydrocarbons such as butane, isobutane, propane or preferably chlorinated and/or fluorinated hydrocarbons.

The present invention also relates to the use of water-soluble polymers of the poly-B-alanine type, such as defined above, in the treatment of hair so as to delay the appearance of an oily aspect.

The present invention also relates to the use, of a combination of a polymer of the poly-B-alanine type and a cosmetic agent such as a polyaspartic acid derivative of Formula III.

The invention principally relates to the use of polymers of the poly-B-alanine type, optionally in combination with polyaspartic acid derivatives, in the form of compositions such as defined above.

The process of treating the hair in accordance with the present invention comprises applying to the hair of an individual having oily hair, the composition defined above, in an amount sufficient to impregnate the hair.

The application is made, for example, immediately after washing the hair with a shampoo, or shortly after shampooing the hair.

After impregnating the hair, especially in the case of a non-rinse composition, the hair can be dried, although it is noted that the hair can be rinsed, if desired, before drying the hair. It is also possible to set the hair before drying it.

The process of treating the hair in accordance with the present invention can also comprise washing the hair with a shampoo containing the composition of the present invention. In this instance it is appropriate, after washing the hair by means of said shampoo, to observe a contact time of a few minutes before rinsing the hair.

The following non-limiting examples are given to illustrate the present invention. In these examples, all parts and percentages are expressed by weight, unless otherwise indicated.

Compound A' has formula III wherein in m=q=r=O,

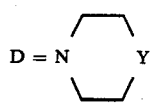

and Y=oxygen. It is described in Example 1 of French Pat. No. 2.403.076.

Compound B' has formula III wherein m=p=q=O and M=Na. It is described in the article by Allen Vegotsky et al, J. of Am. Chem. Soc., 80, pp. 3361–3366, (1958).

Compound C' has formula III wherein in m=p=r=O and Y=—CH$_2$—. It is described in Example 11 of French Pat. No. 2.403.076.

Compound D' has formula III wherein m=p=O, M$^\oplus$ = an ammonium ion derived from monoethanolamine, R'=β-hydroxyethyl and R"=H. It is described in the article by Paolo Neri et al, J. Med. Chem., Vol. 16, No. 3, pp. 893–897, 1973.

Compound E' has formula III wherein in m=p=q=O, and M$^\oplus$=H$^\oplus$. It is described in the articles by K. Kovacs et al, J. Org. Chem., 26, pp. 1084–1091, 1961.

EXAMPLE 1

The following lotion is prepared:

| | |
|---|---|
| Poly-β-alanine, M.W. = 80,000 | 1.0 g |
| Compound A' | 2.0 g |
| Adjuvants (perfume, dye, preservative), sufficient amount | |
| Water, sufficient amount for | 100 g |

The pH is adjusted to 5.0 by the addition of lactic acid.

This composition is employed in the following manner: After a conventional shampoo, the hair is dried and there are applied to the dried hair 8.20 cm$^3$ of the above lotion in a manner so as to impregnate all the hair. The hair is then styled in any conventional manner.

EXAMPLE 2

The following lotion is prepared:

| | |
|---|---|
| Poly-β-alanine, M.W. = 80,000 | 0.5 g |
| Compound B' | 1.5 g |
| Ethyl alcohol at 30% in volume | 25.5 g |
| Adjuvants (perfume, dye, preservative), sufficient amount | |
| Water, sufficient amount for | 100 g |

The pH is adjusted to 7.5 by the addition of 2-amino-2-methyl-1-propanol.

EXAMPLE 3

The following lotion is prepared:

| | |
|---|---|
| Poly-β-alanine, M.W. = 80,000 | 1.0 g |
| Compound B' | 1.0 g |
| Adjuvants (perfume, dye, preservative), sufficient amount | |
| Water, sufficient amount for | 100 g |

The pH is adjusted to 6 by the addition of citric acid.

EXAMPLE 4

The following lotion is prepared:

| | |
|---|---|
| Poly-β-alanine, M.W. = 80,000 | 1.0 g |
| Compound B' | 1.5 g |
| Adjuvants (perfume, dye, preservatives) sufficient amount | |
| Water, sufficient amount for | 100 g |

The pH is adjusted to 6 by the addition of citric acid.

EXAMPLE 5

The following lotion is prepared:

| | |
|---|---|
| Poly-β-alanine, M.W. = 80,000 | 1.0 g |
| Compound C' | 0.5 g |
| Adjuvants (perfume, dye, preservative) sufficient amount | |
| Water, sufficient amount for | 100 g |

The pH is adjusted to 9 by the addition of 2-amino-2-methyl-1-propanol.

EXAMPLE 6

The following pressurized aerosol compostion is prepared:

| | |
|---|---|
| Poly-β-alanine, M.W. = 80,000 | 1.5 g |
| Compound C' | 1.0 g |
| Non-ionic surfactant obtained by condensation of 3.5 mol of glycidol on a C$_{11}$–C$_{14}$ diol, in accordance with French patent 71.17206 (2.091.516) | 0.1 g |
| Adjuvants (perfume, dye, preservative), sufficient amount | |
| Water, sufficient amount for | 100 g |

The pH is adjusted to 5.5 by the addition of 2-amino-2-methyl-1-propanol.

The composition is packaged in a pressurized aerosol container with the following components:

| | |
|---|---|
| Above composition | 85.0 g |
| Chlorofluorocarbon propellant (C.F.C. 114/12; 50/50 by weight) | 15.0 g |
| | 100.0 g |

EXAMPLE 7

The following lotion is prepared:

| | |
|---|---|
| Poly-β-alanine, M.W. = 80,000 | 1.0 g |
| Compound D' | 0.5 g |
| Adjuvants (perfume, dye, preservative), sufficient amount | |
| Water, sufficient amount for | 100 g |

The pH is adjusted to 3 by the addition of lactic acid.

EXAMPLE 8

The following lotion is prepared:

| | |
|---|---|
| Poly-β-alanine, M.W. = 80,000 | 2.0 g |
| Compound D' | 1.0 g |
| Ethanol, 20% | 17.0 g |
| Adjuvants (perfume, dye, preservative), | |

| | |
|---|---|
| sufficient amount | |
| Water, sufficient amount for | 100 g |

The pH is adjusted to 5.3 by the addition of lactic acid.

EXAMPLE 9

The following lotion is prepared:

| | |
|---|---|
| Poly-β-alanine, M.W. = 80,000 | 1.5 |
| Compound E' | 1.5 g |
| Adjuvants (perfume, dye, preservative) sufficient amount | |
| Water, sufficient amount for | 100 g |

The pH is adjusted to 3.5 by the addition of citric acid.

EXAMPLE 10

The following lotion is prepared:

| | |
|---|---|
| Poly-β-alanine, M.W. = 80,000 | 1.5 g |
| Compound E' | 0.5 g |
| Ethanol, 20% | 17.0 g |
| Adjuvants (perfume, dye, preservative), sufficient amount | |
| Water, sufficient amount for | 100 g |

The pH is adjusted to 4.5 by the addition of 2-amino-2-methyl-1-propanol.

EXAMPLE 11

The following lotion is prepared:

| | |
|---|---|
| Poly-β-alanine, M.W. = 80,000 | 0.5 g |
| Compound C' | 0.5 g |
| Adjuvants (perfume, dye, preservatives), sufficient amount | |
| Water, sufficient amount for | 100 g |

The pH is adjusted to 5 by the addition of HC.

EXAMPLE 12

The following lotion is prepared:

| | |
|---|---|
| Poly-β-alanine, M.W. = 80,000 | 1.5 g |
| Perfume, sufficient amount | |
| Dye, sufficient amount | |
| Ethyl alcohol, sufficient amount for 20%, by volume | |
| Water, sufficient amount for | 100 g |

This non-rinse lotion is applied to oily hair after shampooing. It imparts to the hair good cosmetic properties and delays the return of an oily aspect.

EXAMPLE 13

The following shampoo composition is prepared:

| | |
|---|---|
| Poly-β-alanine, M.W. = 80,000 | 3 g |
| Non-ionic surfactant obtained by condensation of 3.5 mol of glycidol on a $C_{11}$-$C_{14}$ α-diol | 0.1 g |
| Adjuvants (perfume, dye, preservative), sufficient amount | |
| Water, sufficient amount for | 100 g |

EXAMPLE 14

The following after-shampoo lotion is prepared:

| | |
|---|---|
| Poly-β-alanine, M.W. = 80,000 | 2.5 g |
| Perfume, sufficient amount | |
| Dye, sufficient amount | |
| Water, sufficient amount for | 100 g |
| This after-shampoo lotion delays the appearance of an oily aspect of the hair. | |

What is claimed is:

1. A non-rinse cosmetic composition for the hair to delay the appearance of an oily aspect of the hair comprising (i) a water soluble polymer comprising 50 to 100% of units of the formula $-\!(CH_2-CH_2-CO-NH)\!-$ and from 0 to 50% of units of the formula

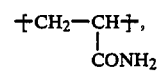

said water soluble polymer having a molecular weight ranging from 500 to 200,000 and being present in an amount effective to delay the appearance of an oily aspect of the hair, and (ii) a polyaspartic derivative having the formula:

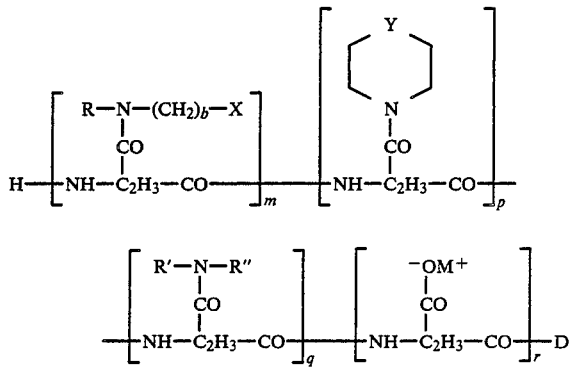

wherein

R represents hydrogen or lower alkyl, b is a whole number ranging from 2 to 6,

X represents $-NR_I(R_{II})$ or $\oplus-NR_I(R_{II})(R_{III})Z^\ominus$ wherein $R_I$, $R_{II}$ and $R_{III}$ each independently represent hydrogen, alkyl having 1-18 carbon atoms or alkenyl having at most 18 carbon atoms and $Z^\ominus$ represents an anion derived from an organic or mineral acid;

Y represents oxygen, methylene, $-N(R''')-$ or $-N(R''')(R'''')Z_1^\ominus$ wherein R''' and R'''' each independently represent hydrogen, alkyl having 1-18 carbon atoms or alkenyl having at most 18 carbon atoms and $Z_1^\ominus$ represents an anion derived from an organic or mineral acid;

R' represents hydrogen, lower hydroxyalkyl, lower hydroxyalkyloxyalkyl, alkyl having 1-18 carbon atoms or alkenyl having at most 18 carbon atoms;

R" represents hydrogen, lower hydroxyalkyl or lower alkyl;

M represents hydrogen, alkali metal, ½ alkaline earth metal atom or M+ represents an ammonium ion derived from an amine having the formula, $HN(R)-(CH_2)_b-X$,

or HN(R')—R" wherein R, b, X, Y, R' and R" have the meanings given above,

D represents

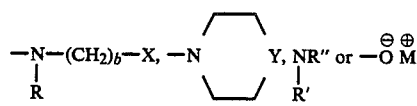

or $-O^\ominus M^\oplus$ wherein R, b, X, Y, R', R" and M have the meanings given above, m, p, q and r each represent a whole number including zero, such that the sum (m+p+q+r) ranges from 15 to 500, m and p being able to be zero simultaneously only when (a) q is other than zero and R' represents hydroxyalkyl and (b) q is equal to zero in an aqueous carrier.

2. The cosmetic composition of claim 1 wherein said polymer is present in an amount ranging from 0.1 to 5 percent by weight bases on the total weight of said composition.

3. The cosmetic composition of claim 1 wherein said polymer is present in an amount ranging from 0.5 to 2 percent by weight based on the total weight of said composition.

4. The cosmetic composition of claim 1 wherein said polyaspartic acid derivative is present in an amount ranging from 0.1 to 5 percent by weight based on the total weight of said composition.

5. The cosmetic composition of claim 1 wherein said polyaspartic acid derivative is present in an amount ranging from 0.2 to 2 percent by weight based on the total weight of said composition.

6. The composition of claim 1 packaged in a pressurized container in combination with a propellant.

7. A process for treating the hair of an individual having oily hair comprising applying to said hair a sufficient amount to impregnate said hair of a non-rinse cosmetic composition containing:

(i) from 0.1 to 5 percent by weight of a water soluble polymer comprising 50 to 100% of unit of the formula $-CH_2-CH_2-CONH-$ and from 0 to 50% of units of the formula

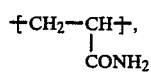

said water soluble polymer having a molecular weight ranging from 500 to 200,000, and (ii) from 0 to 5% by weight of a polyaspartic acid derivative having the formula:

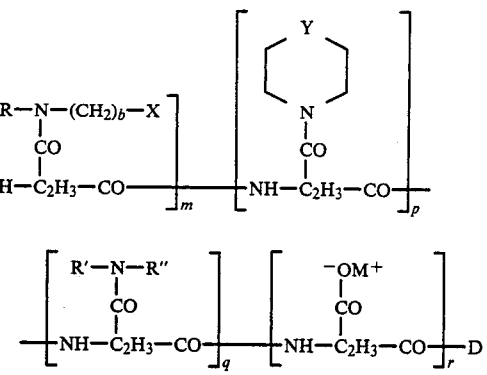

wherein

R represents hydrogen or lower alkyl, b is a whole number ranging from 2 to 6,

X represents $-NR_I(R_{II})$ or $\oplus-NR_I(R_{II})(R_{III})Z^\ominus$ wherein $R_I$, $R_{II}$ and $R_{III}$ each independently represent hydrogen, alkyl having 1-18 carbon atoms or alkenyl having at most 18 carbon atoms and $Z^\ominus$ represents an anion derived from an organic or mineral acid, Y represents oxygen, methylene, —N(R''')— or —N(R''')(R'''')$Z_1^\ominus$ wherein R''' and R'''' each independently represent hydrogen, alkyl having 1-18 carbon atoms or alkenyl having at most 18 carbon atoms and $Z_1^\ominus$ represents an anion derived from an organic or mineral acid;

R' represents hydrogen, lower hydroxyalkyl, lower hydroxyalkyloxyalkyl, alkyl having 1-18 carbon atoms or alkenyl having at most 18 carbon atoms;

R" represents hydrogen, lower hydroxyalkyl or lower alkyl;

M represents hydrogen, alkali metal, ½ alkaline earth metal atom or M+ represents an ammonium ion derived from an amine having the formula, $HN(R)-(CH_2)_b-X$,

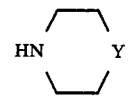

or HN(R')—R" wherein R, b, X, Y, R' and R" have the meanings given above,

D represents

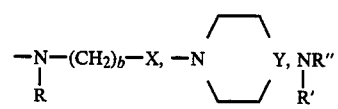

or $-O^\ominus M^{61}$ wherein R, b, X, Y, R', R" and M have the meanings given above, m, p, q and r each represent a whole number including zero, such that the sum (m+p+q+r) ranges from 15 to 500, m and p being able to be zero simultaneously only when (a) q is other than zero and R' represents hydroxyalkyl and (b) q is equal to zero in an aqueous carrier.

* * * * *